(12) United States Patent
Castleberry et al.

(10) Patent No.: US 11,129,990 B2
(45) Date of Patent: Sep. 28, 2021

(54) DELIVERY SYSTEM FOR INTRACORPOREAL SMOOTH MUSCLE STIMULATION

(71) Applicant: Allotrope Medical, LLC, Houston, TX (US)

(72) Inventors: Jeffrey Paul Castleberry, Longmont, CO (US); Nishant Verma, Houston, TX (US); Albert Yung-Hsiang Huang, Houston, TX (US)

(73) Assignee: Allotrope Medical, LLC, Houston, TX (US)

( * ) Notice: Subject to any disclaimer, the term of this patent is extended or adjusted under 35 U.S.C. 154(b) by 0 days.

(21) Appl. No.: 16/420,809

(22) Filed: May 23, 2019

(65) Prior Publication Data

US 2019/0275323 A1    Sep. 12, 2019

Related U.S. Application Data

(63) Continuation of application No. PCT/US2017/063428, filed on Nov. 28, 2017.

(60) Provisional application No. 62/511,301, filed on May 25, 2017, provisional application No. 62/489,389, (Continued)

(51) Int. Cl.
*A61N 1/36* (2006.01)
*A61N 1/05* (2006.01)
*A61N 1/40* (2006.01)
*A61B 5/00* (2006.01)

(52) U.S. Cl.
CPC ............ *A61N 1/3615* (2013.01); *A61N 1/05* (2013.01); *A61N 1/3606* (2013.01); *A61N 1/36007* (2013.01); *A61N 1/36017* (2013.01); *A61N 1/36034* (2017.08); *A61N 1/36042* (2013.01); *A61N 1/36132* (2013.01); *A61N 1/40* (2013.01);
(Continued)

(58) Field of Classification Search
CPC .............. A61N 1/3615; A61N 1/36007; A61N 1/3606; A61N 1/36132; A61N 1/36135; A61N 1/36034; A61N 1/36017
See application file for complete search history.

(56) References Cited

U.S. PATENT DOCUMENTS 3,662,758 A * 5/1972 Glover ............... A61N 1/36007
                                                607/40
4,535,771 A    8/1985 Takayama
5,010,895 A    4/1991 Maurer et al.
(Continued)

FOREIGN PATENT DOCUMENTS

| EP | 2684525 A1 | 1/2014 |
| WO | WO-2015123441 A1 | 8/2015 |
| WO | WO-2018098468 A1 | 5/2018 |

OTHER PUBLICATIONS

European Supplemental Search Report dated Dec. 3, 2019 for EP17873428.

*Primary Examiner* — Paula J Stice
(74) *Attorney, Agent, or Firm* — Wilson Sonsini Goodrich & Rosati

(57) ABSTRACT

An electrical stimulation system includes a stimulator having at least one electrode and a power supply. The electrode is connectable to the power supply, and the power supply delivers electrical stimulation energy in the form of a capacitive discharge voltage through the stimulator and electrode to tissue proximate a target anatomy to induce an observable response in the target anatomy during a medical procedure.

25 Claims, 8 Drawing Sheets

Related U.S. Application Data filed on Apr. 24, 2017, provisional application No. 62/426,974, filed on Nov. 28, 2016.

(52) U.S. Cl.
CPC ......... *A61B 5/4041* (2013.01); *A61B 2505/05* (2013.01); *A61N 1/36135* (2013.01)

(56) References Cited

U.S. PATENT DOCUMENTS

| | | |
|---|---|---|
| 6,292,701 B1 | 9/2001 | Prass et al. |
| 7,877,152 B2 | 1/2011 | Chu |
| 8,954,153 B2 | 2/2015 | Boggs, II |
| 2009/0247817 A1 | 10/2009 | Forsell |
| 2011/0301662 A1 | 12/2011 | Bar-Yoseph et al. |
| 2012/0101326 A1 | 4/2012 | Simon et al. |
| 2015/0005841 A1 | 1/2015 | Pal et al. |
| 2017/0042445 A1* | 2/2017 | Huang .................. A61B 5/425 |

* cited by examiner

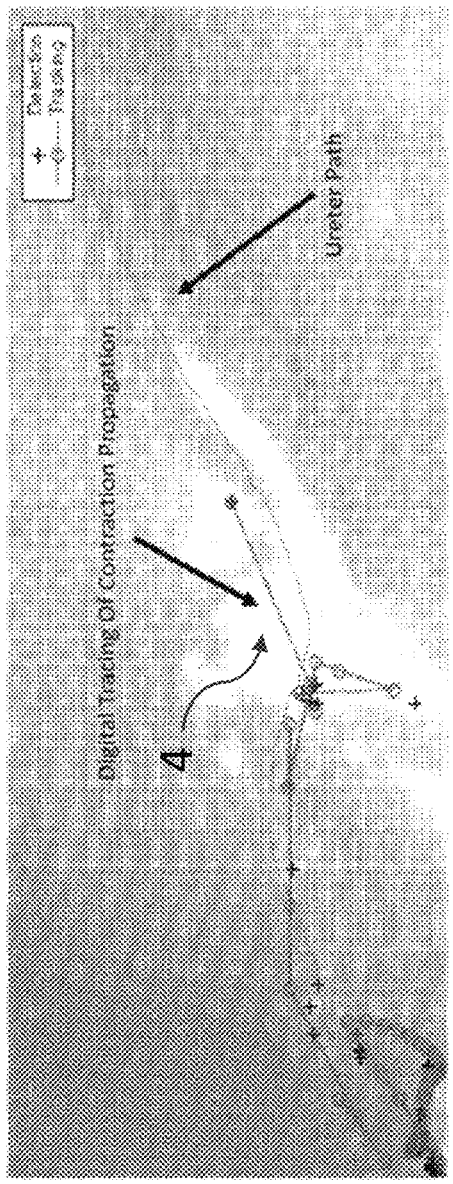
FIG._2
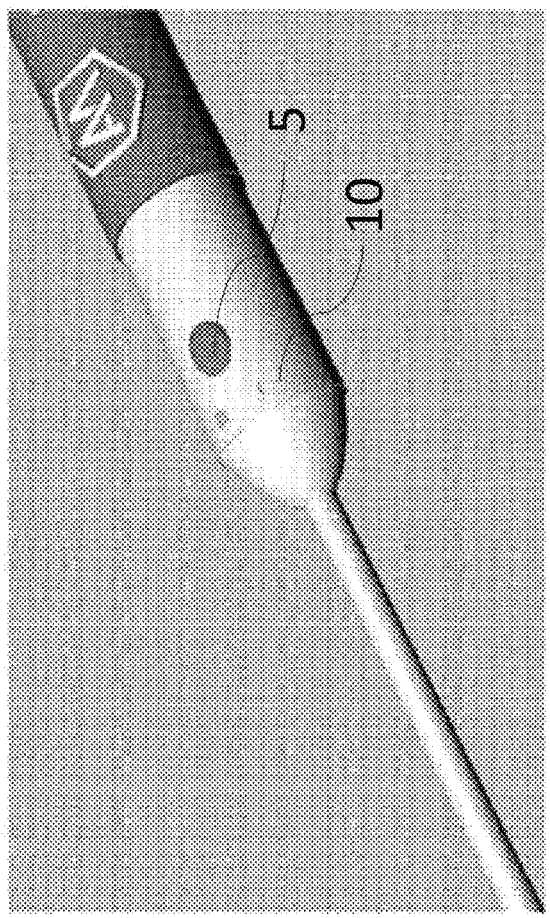
FIG._3

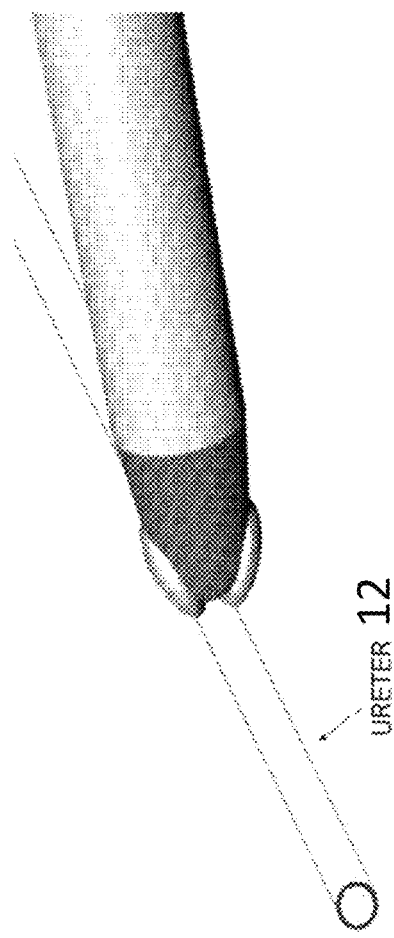
FIG._6
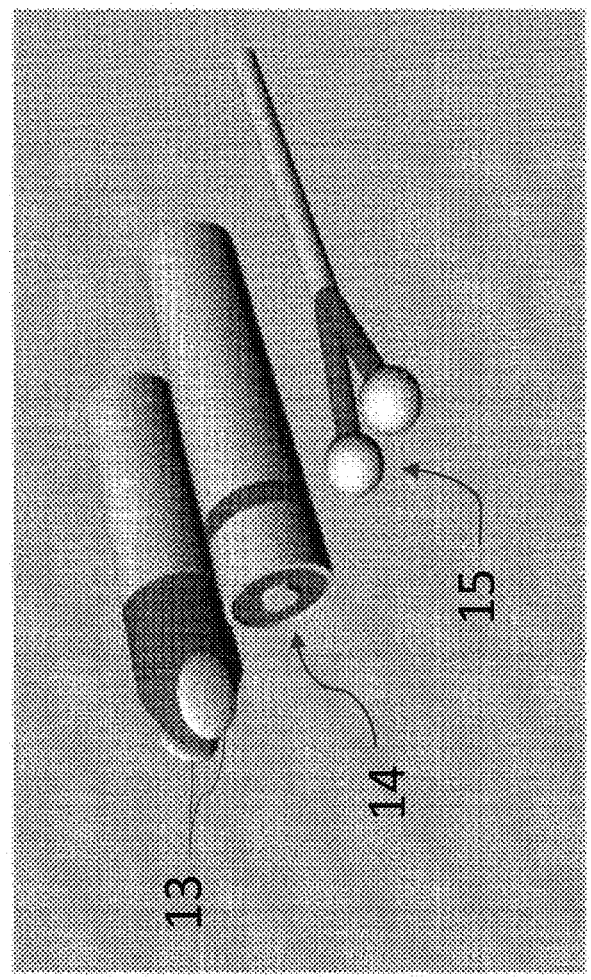
FIG._7

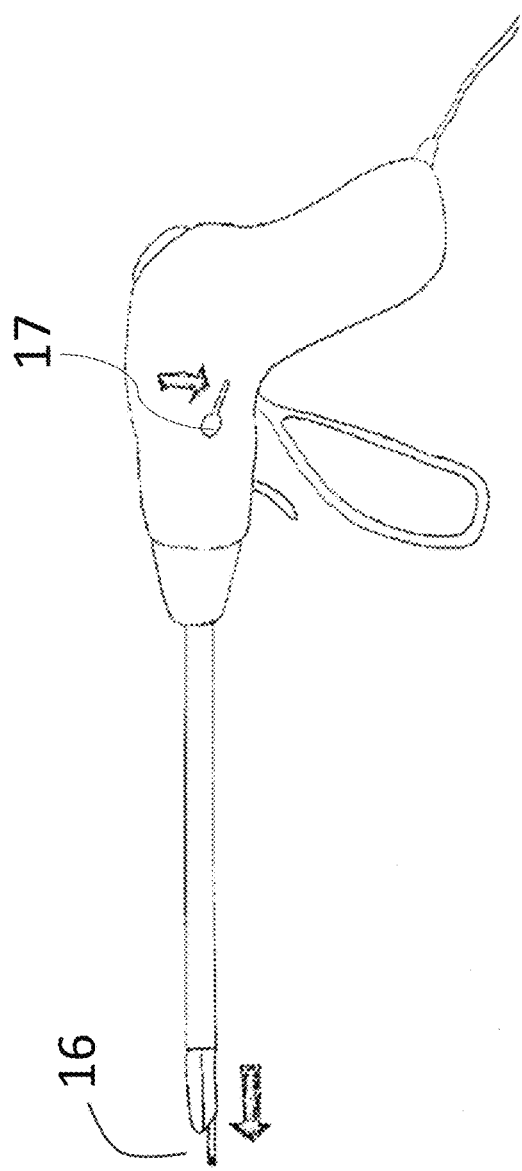
FIG._8
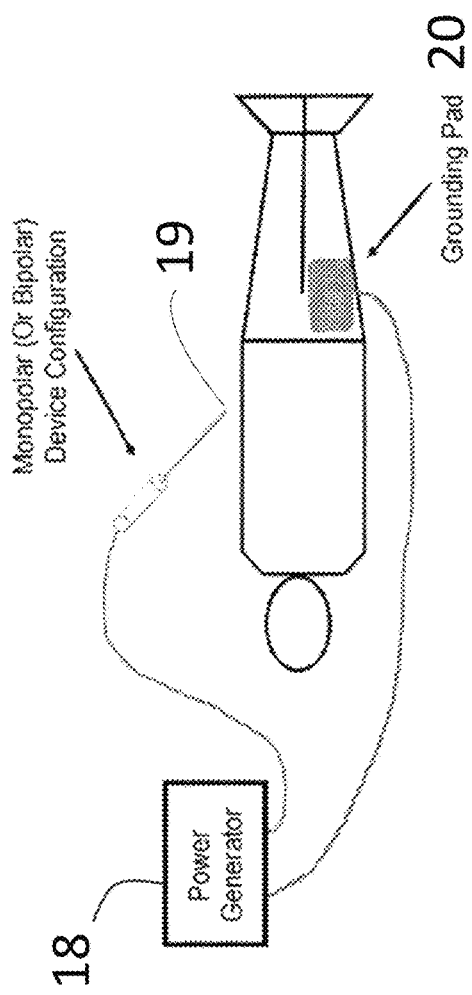
FIG._9

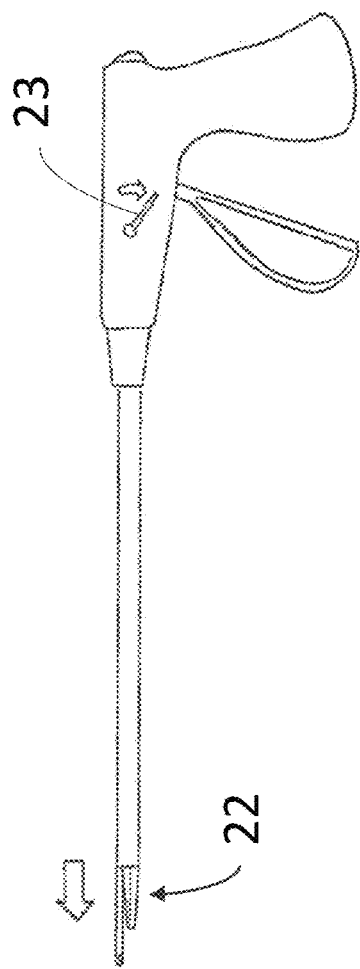
FIG._11
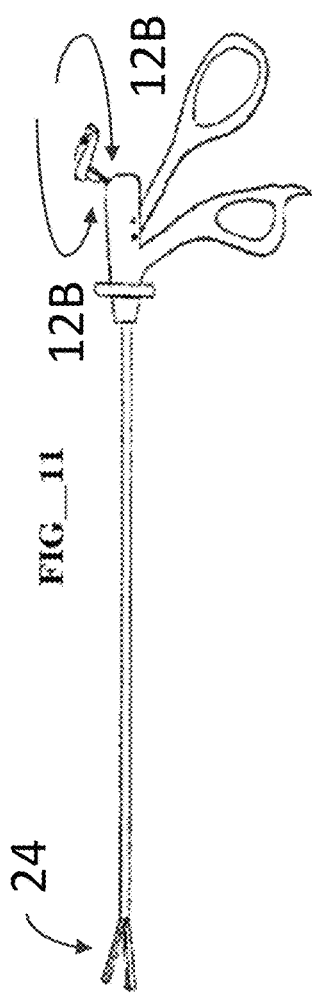
FIG._12A
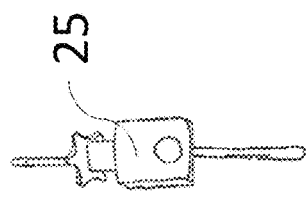
FIG._12B

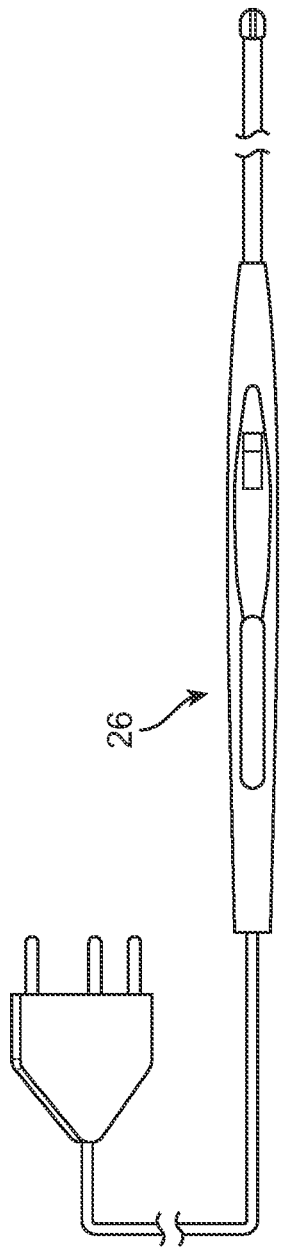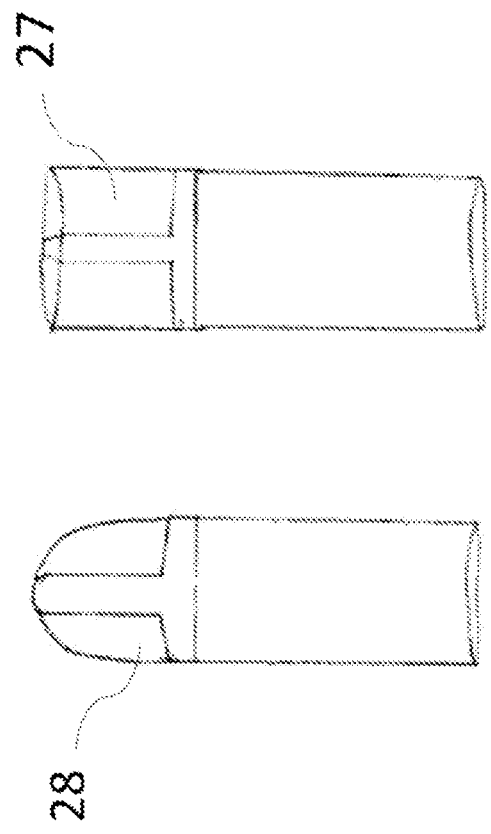
FIG. 13
FIG. 14A    FIG. 14B

DELIVERY SYSTEM FOR INTRACORPOREAL SMOOTH MUSCLE STIMULATION

CROSS-REFERENCE TO RELATED APPLICATIONS

This application is a continuation of PCT Application No. PCT/US2017/63428, filed Nov. 28, 2017, claims the benefit of the following prior provisional applications: U.S. Provisional No. 62/511,301, filed May 25, 2017; U.S. Provisional No. 62/489,389, filed Apr. 24, 2017; and U.S. Provisional No. 62/426,974, filed Nov. 28, 2016, the full disclosures of which are incorporated herein by reference.

BACKGROUND OF THE INVENTION

1. Field of the Invention

This invention relates generally to medical apparatus and methods, and more particularly to a system for stimulating contraction of intracorporeal smooth muscles.

The field of minimally invasive surgery has been around for a relatively short amount of time, and only in the last two decades have even common procedures such as gallbladder removal and appendix removal shifted to minimally invasive approaches as being the gold standard. To adapt to this new approach in operating on patients, instruments need to change from traditional configurations to distinctly different shapes and parameters. In addition, interfacing remotely with tissues within the human chest and abdomen also require procedure changes from not only traditional methods of repair, but even tissue identification methods as tactile feedback is largely lost requiring increased reliance on visual indicators of structures and tissue consistency.

The human abdomen and pelvis has two distinct types of muscle within it. Skeletal muscle is the muscular tissue that can be voluntarily controlled, and connects bony structures together for movement. Smooth muscle is under involuntary (autonomic control) and is found in gastrointestinal tissues such as the stomach, colon and small intestine. It is also found in parts of the urologic system such as the ureter and bladder, as well as the thoracic cavity including the esophagus. In the ureter and intestines these tissues contract in a pulsatile way under nervous system control. In the case of the ureter as well as intestines, the body spontaneously generates the initial signal at the proximal point (e.g.—the stomach, or the kidney) and then the tissues naturally continue to propagate this contraction down the entire length of the organ. On a sub-cellular level, this threshold of contraction triggering in intestinal tissue is known as the slow-wave threshold, and initiation begins typically in tissues known as pacemaker regions. Unique to the ureter, propagation of the full-length contraction begins at the renal pelvis with a ring-like contraction at the ureteropelvic junction as a response to urine filling.

In a physiologic state, the muscles of the body (smooth and skeletal) are typically both triggered and controlled by nerves and nervous tissue. Through electrical signaling, the muscle tissue responds. This response, as well as the ability to stimulate muscles through stimulating nerves is used widely in non-invasive approaches as well as in traditionally open (non-minimally invasive and non-robotic) procedures with a medical focus almost exclusively on nerves and skeletal muscle tissue. In the field of Anesthesia, facial nerve stimulation via electrodes applied manually to the skin is performed as a way to determine if chemical paralytic agents are at efficacious levels. In the fields of Orthopedic surgery and Otolaryngology, handheld stimulators are applied to nerves in an exposed forearm or hand to identify what muscle it controls, and in the neck, what muscles are innervated by nerves as they are being dissected out.

Smooth muscle electrical stimulation for anatomical identification in surgery has not been implemented in either open, minimally invasive or robotic settings. Today, there are other smooth muscle stimulation applications including implanted devices that stimulate sacral nerves (and by extension the bladder) to decrease hyperactivity of the target tissue, and devices implanted to interrupt nerve signaling to the stomach in an effort to decrease nausea and vomiting in gastroparesis patients. Otherwise, electrical smooth muscle stimulation as a way to identify (or to confirm the identity of) target tissues, or distinguish between smooth muscle and surrounding tissue, or differentiate between functional and non-functional tissue by location, or generate a tissue response is a technique that is neither taught, or applied in the field of surgery in open, minimally invasive or robotic approaches.

During a minimally invasive operation, the surgeon relies heavily on visual indicators to determine tissue type, expected textures and density, as well as intracorporeal landmarks to determine where to and not to make incisions and resections. With the real time image being projected on a video monitor, there are many viewing limitations such as a fixed field of view, two-dimensional image, meanwhile the surgeon needs to be aware of critical tissues and structures beyond the area projected onto the video screen. As such, a surgeon is reliant on their physical, operative capabilities for safe tissue handling, operative experience for aberrant structures/anatomy, and on their assistant(s) to safely project a field of view that lets them operate effectively on the patient's behalf.

Intestinal tissues are easy to identify and manipulate in the minimally invasive environment because they are not covered by other tissues such as peritoneum, and so are other smooth muscle structures such as the stomach. The ureter poses a different set of unique challenges in the minimally invasive environment because it resides behind the peritoneum, traverses anatomic areas such as the pelvic brim (where it descends under tissue layers, out of immediate view), and has several other critical structures above and below it, obscuring it's direct identification, including major vasculature, colon, and gynecologic anatomy that often require surgical addressment of their pathology or temporary retraction for accessibility.

As such, identification of the ureters can quickly become challenging in this unique setting, especially in the minimally invasive environment where the surgeon relies on long instruments to manipulate and cut critical tissues. Currently there are only two predominant methods used to both identify and protect the human ureter in minimally invasive surgery. First, another medical specialist, a Urologist, may be called in to the operating room to place stiff plastic stents retrograde through the bladder and into the ureters to stiffen them in an effort to make them more visible on the video screen during the operation. The plastic stents are also brightly colored, so if there is a cut or transection to the ureter this results in the plastic being seen on the video screen so that the injury can be addressed during the same operation. Second, the other method is for the surgeon to perform careful and meticulous dissection to visibly expose the ureter for disassociating it from surrounding tissues. This approach can be risky, especially if there is scarring or inflammation further obscuring the ureter, where it is difficult to visualize or identify, and as such, the dissection itself risks injury.

There exists a need to be able to identify the ureter in this unique setting of minimally invasive surgery where dissection can be minimized, and where alternatives such as stent placement may not be viable or economically preferable options. In tandem, direct smooth muscle stimulation in a minimally invasive setting in any of the major cavities (thoracic, abdominal, pelvic) of the body is a process that can greatly benefit the operating physician in terms of target tissue identification, reducing procedure time and patient morbidity, and which is an approach that has not heretofore been implemented in a surgical setting as an adjunct surgical technique.

These objectives are at least partly addressed by the probe and method described in WO2015/123441, having a common inventor with the present application. The probe has bipolar electrodes at its tip which are used to apply a stimulation current to tissue in the vicinity of the patient's ureter. The location of the ureter can be visually determined by observing contraction of the ureter in response to the applied stimulation current. While a significant advance over prior previous methods for observing and protecting the ureter as discussed above, the probes and methods described in WO2015/123441 represent a first generation technology. It would be desirable to provide improved methods and apparatus which are compatible with additional procedures and anatomies, with additional laparoscopic and other surgical tools, and which perform in a more controlled and efficient manner.

2. Description of the Background Art

WO2015/123441 is discussed above. See also US2009247817; U.S. Pat. Nos. 8,954,153; 7,877,152; and 6,292,701.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

The system of the present invention uses brief electrical impulses applied directly to the target muscle to induce contractile wave propagation in smooth muscle found in the thoracic, abdominal or pelvic spaces in the body, such as in tissue of the ureter. As detailed in the background above, all muscle tissue fundamentally contracts based on electrical signals that exist naturally in the body. The systems of the present invention rely in part on the discovery that in certain smooth muscles, such as the ureter, the contractile wave propagation does not have to be unidirectional as it is in natural physiologic cases. The systems of the present invention function by direct stimulation of smooth muscle autonomic function, and not on nerve stimulation, to trigger a contractile muscle response. By stimulating the muscle directly, the systems and methods of the present invention can achieve a highly specific response in a target anatomy, such as the ureter.

In a first aspect, the present invention provides a method for inducing an observable response in a targeted anatomy, typically during a medical procedure. The method comprises providing an electrical stimulator, typically a probe-type stimulator having a shaft with at least one electrode at the distal end thereof. Electrical stimulation energy is delivered from the stimulator to tissue proximate to the target anatomy, wherein such stimulation energy comprises a capacitive discharge of an initial voltage. The target anatomy can be observed by visually or otherwise detecting a response in the tissue induced by the stimulation energy, typically a contractile response where the target anatomy can be observed to move or otherwise change its orientation in the visual field. In this way, fragile anatomies, such as the ureter, which are subject to damage may be visualized and avoided during a surgical procedure. Alternatively, in some instances, it may be desirable to identify the target anatomy to facilitate a surgical or other treatment.

While the methods of the present invention will often utilize a standalone probe or other device, it will be appreciated that electrodes and other electrical stimulating elements may be incorporated into surgical devices so that the surgical device can itself be used to detect the target anatomy prior to performing a surgical procedure. In still other instances, it may be possible to deliver the stimulating energy without using a solid electrode, such as by using electrically conductive fluids, plasmas, or the like.

The capacitive discharge may be "driven," e.g. controlled to a specific decay shape regardless of tissue resistance, or "undriven." The preferred embodiment is an undriven capacitive discharge. By "undriven" capacitive discharge, it is meant that an initial charge discharges with an exponential waveform having a time constant equal to the product of controlled capacitance and uncontrolled tissue resistance, as shown in FIG. 4 with the label "Capacitor Discharge Wave."

In exemplary embodiments of the methods herein, the undriven capacitive discharge will have a peak voltage in the range from 5 V to 500 V, preferably from 6 V to 60 V. The capacitive discharge will further preferably have a resultant variable current less than 1 A, usually being in the range from 5 mA to 125 mA. The actual value will be the result of the voltage and charge combined with the actual tissue resistance at the point of stimulation. Still further, the undriven capacitive discharge will usually be greater than 30 µC, preferably being the range from 40 µC to 450 µC. The undriven capacitive discharge will still further preferably have a resultant total energy greater than about 0.05 mJ, preferably being in the range from 0.05 mJ to 9 mJ. The actual value will be the result of the voltage and charge combined with the actual tissue resistance at the point of stimulation. In still further instances, the capacitive discharge will usually have a duration in the range from 10 µs to 20 ms, typically being in the range from 100 µs to 1.5 ms. Additionally, when the undriven capacitive discharge is delivered in a continuous string of pulses, it is usually delivered at a range from 0.1 Hz to 2 Hz, preferably being from 0.5 Hz to 1 Hz.

The exemplary target anatomy is the ureter which is to be protected during a variety of laparoscopic and open surgical procedures in and near the bladder. Other target anatomies include the esophagus, stomach, bladder, and intestine due to their smooth muscle composition in which the procedures may be used to distinguish between functional and diseased tissue within the organ, or the like.

In other specific embodiments of the methods herein, the parameters of the undriven capacitive discharge will be adjustable by a user before and during a procedure. In other instances, the parameters of the undriven capacitive discharge will be preset so that the user will not be able to adjust such parameters before or during the procedure. In many instances, the capacitive discharge will be bipolar, while in other instances the capacitive discharge may be monopolar, typically being applied by a single electrode while the patient is wearing a conventional dispersive or grounding electrode at a location remote from the surgical site (FIG. 9). In still other instances, the stimulator may comprise a shaft which may be advanced through a trocar, typical in laparoscopic surgery or through a working endoscope's working channel, typical of other endoscopic procedures or through a catheter lumen, typical of other catheter procedures. In certain alternative instances, a shaft or other component of the stimulator may be advanced through or concurrently with a surgical tool, while in still other instances, the shaft may be grasped and advanced using graspers or other conventional surgical tools in both open and laparoscopic procedures. In yet further instances, the shaft or other component of the stimulator may be advanced by a robot arm or other component in robotic surgical procedures.

In a second aspect of the present invention, an electrical stimulation system comprises a stimulator and a power supply. The stimulator includes at least one electrode, often comprising two electrodes for use in bipolar procedures, and the power supply is connectible to the at least one electrode and configured to deliver electrical stimulation energy through the stimulator to tissue proximate a target tissue now anatomy. The stimulation energy produced by the power supply comprises a capacitive discharge waveform, and the electrical stimulation system is useful for inducing observable responses in a target anatomy according to any of the methods above.

In specific instances, the power supply is configure to elicit a peristaltic or contractile response in a ureter when the at least one electrode is positioned to deliver the stimulatory energy to tissue proximate the ureter.

In preferred embodiments, the power supply is configure to deliver an undriven capacitive discharge, and the undriven capacitive discharge has a peak voltage in the range from 5 V to 500 V, preferably in the range from 6 V to 60 V. The undriven capacitive discharge is further preferably a resultant variable current less than 1 A, typically being in the range from 5 mA to 125 mA. The actual value will be the result of the voltage and charge combined with the actual tissue resistance at the point of stimulation. Still further, the undriven capacitive discharge will typically be greater than 30 μC, usually being in the range from 40 μC to 450 μC. Usually, each undriven capacitive discharge will deliver a total resultant energy greater than 0.05 mJ, typically being in the range from 0.05 mJ to 9 mJ. The actual value will be the result of the voltage and charge combined with the actual tissue resistance at the point of stimulation. Still further, the undriven capacitive discharge will usually have a duration in the range from 10 μs to 20 ms, usually begin in the range from 100 μs to 1.5 ms. The electrical stimulation system may be configured to allow for manual or automatic capacitive discharges at a rate from 0.1 Hz to 2 Hz, typically from 0.5 Hz to 1 Hz.

The electrical stimulation systems may be configure to allow for a user to adjust the discharge parameters, but in other instances may be configured so that all discharge parameters are preset without the opportunity for user adjustment.

The stimulator itself may be configured in any of the arrangements described above with respect to the methods herein. In particular, the electrodes may be monopolar, bipolar, and the stimulator may be configured to be advanced through a trocar, cannula, an endoscope, or a catheter, be advanced through or concurrently with a surgical tool, be configured to be advanced using graspers, be configured to be advanced by a robotic arm or system, and the like.

Still further, the electrical stimulator may include a handle, and the power supply may be disposed inside the handle with power being provided by a rechargeable or other battery. Alternatively, the power supply may be configured within a tabletop unit which is connected to the probe or other electrical stimulator by a tether cord.

BRIEF DESCRIPTION OF THE DRAWINGS

FIG. 2—Digital tracking and recognition of the ureter's pathway and propagating contractile wave using computer vision. Software system can trace the ureter's path and provide graphic overlay to represent this path even after the contraction has subsided.

FIG. 3—Handle details of system with visual indicators for power and impulse delivery along with button to deliver impulse.

FIG. 6—Bipolar device tip interfacing with ureter for stimulation. End effector electrodes are separated by nonconductive material.

FIG. 7—Bipolar device tip variants with a cathode and anode component to each.

FIG. 8—Device integrated into existing electrosurgical tool and extendable/retractable with a lever on the handle to ensure clear separation between stimulation impulse delivery and electrocautery energy delivery into tissues.

FIG. 9—A monopolar device configuration powered via remote electrical generator and controller with tethered hand held component and a dispersive or grounding pad.

FIG. 11—Device embodiment with stimulator incorporated into surgical electrosurgical, grasper, and/or dissector tools.

FIGS. 12A and 12B—Device embodiment with grasper/dissector tools where the jaws of the distal end of the instrument function as an anode and cathode.

FIG. 13—Device embodiment where the handle, button and instrument shaft with end effector at distal tip are tethered to and powered by an off-field generator via a plug-in system.

FIGS. 14A and 14B—Device embodiment with electrodes separated from each other, having maximal surface area for optimized impulse delivery into tissues, and distal tip lacking sharp edges.

DETAILED DESCRIPTION OF THE INVENTION

Figure 1:
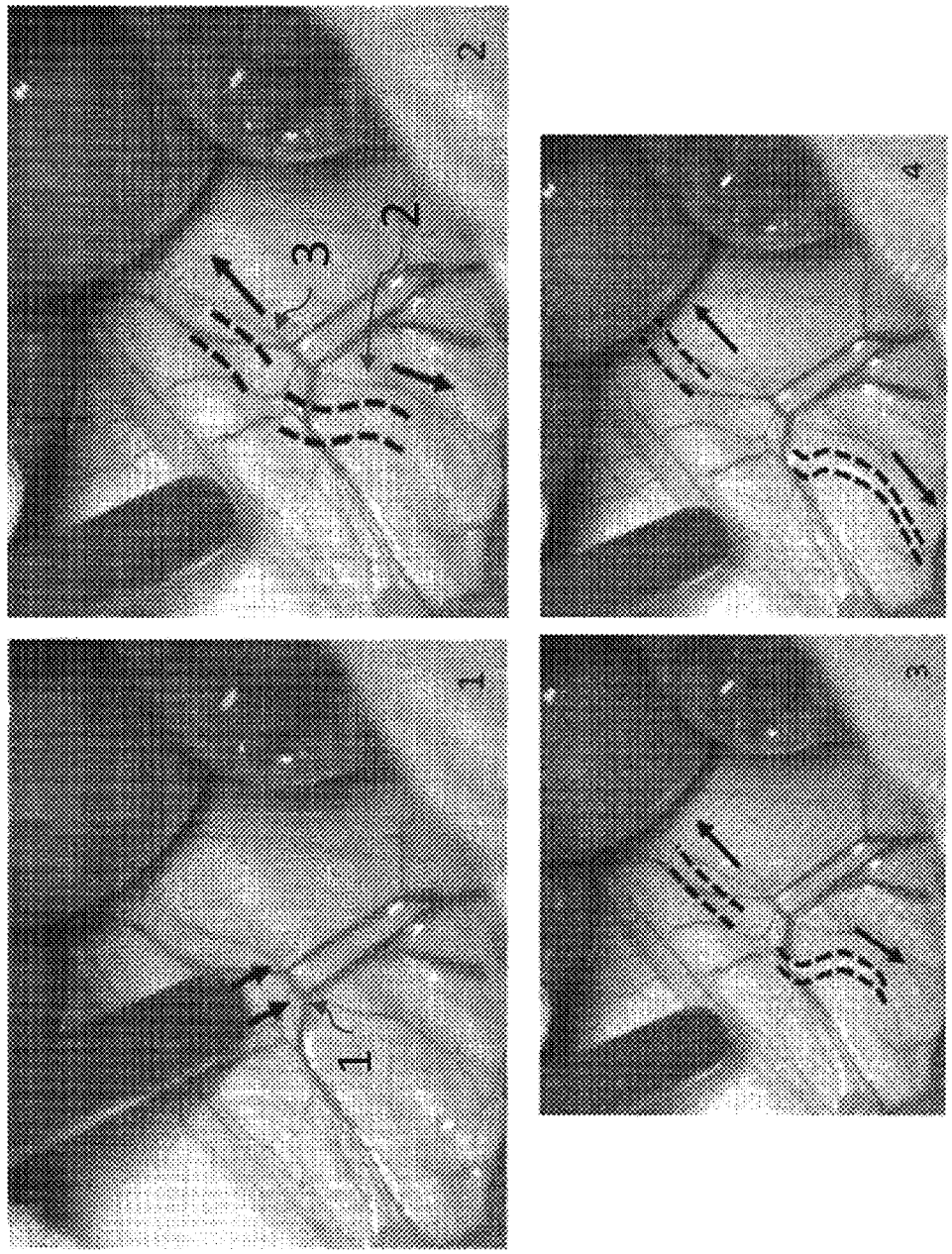
FIG. 1—Images showing the point of stimulation of the ureter and the subsequent propagating contractions that progress antegrade and retrograde away from the functional tip of the novel device.

With the system of the present invention, electrical stimulation of the ureter in-vivo at any point along its length in the body results in a reliable and reproducible bi-directional, visible contractile wave (FIG. 1) that allows the operator to quickly and reliably visualize its path on the operating video screen during minimally invasive surgery, as well as under direct visualization in an open abdomen operating field. A full-length contractile wave that propagates from the point of stimulation 1 in both directions (antegrade 2 and retrograde 3) occurs, no matter at what point on the ureter the stimulatory effect is applied. This wave propagation of ureter movement provides direct visual indication of the structure's location and functionality.

Especially in cases of tortuous or often non-linear ureter paths with structures deviating from their natural positions either temporarily during surgical manipulation or due to a pathologic state, the visualization of ureter movement and therefore knowledge visualization of the path the ureter takes is critical to patient safety as it allows the surgeon to identify and avoid injury of this structure during surgery. This unique tissue response is distinctly non-physiologic, as the ureter's smooth muscle contractile wave propagation is normally unidirectional; emanating from the kidney and progressing towards the bladder.

In tandem, the propagation waves of contraction that progresses bi-directionally (from the point of novel stimulation) would occur at a velocity of approximately 2 to 6 centimeters per second. This is a unique characteristic of ureteral tissue contractile wave propagation. With this understanding, in one version of the system of the present invention, a computer vision system can automatically recognize tissue contractions at these speeds, and digitally project the path the tissue takes on the video monitor used by the operating physician to see the operative field (FIG. 2). In this approach, a digital representation of the ureter's location and path 4 will be on-screen for intuitive localization of this tissue. This may or may not require the handheld portion of the system of the present invention to be connected to a digital processing component off of the surgical field. The digital tracing of the ureter's path would remain on-screen for a set amount of time to serve as a visual reminder of where the structure is while the surgeon continues their operation, and then disappear to minimize potential obscuring of the operative field of view.

The system of the present invention is also designed in such a way to function uniquely in the minimally invasive environment, and can easily be used in surgical procedures where tissues are visualized directly as well. The system is can either be held by an operator, or be grasped by an operating assistant (human or mechanical) as it is a linear device with an extended shaft to ensure ease of passage through laparoscopic ports that traverse the human body wall, and serve as airtight access points into the enclosed abdomen. Shaft length may be as long as 45 centimeters for use in patients with a larger body habitus. The width of the instrument shaft will be less than 6 millimeters wide. This allows the device to function in the thoracic, abdominal and pelvic spaces to stimulate target tissues in a minimally invasive setting as well as easily be applicable in open surgeries with a shorter shaft length for ease of maneuverability. The shaft may be rigid, curved, flexible or malleable to be shaped by the physician during clinical use.

The end of the instrument to be held by the operator or operating assistant is to be held naturally in a pencil grip, or palm grip. In one preferred embodiment, this end will be shaped in a tubular fashion similar to a marker or large pencil. The actuating button 5 that triggers voltage and current pulse delivery positioned in such a way to be able to be pressed with the finger or thumb of either the left or right hand (FIG. 3). Depressing the button delivers an electrical impulse of short duration, as the system is designed to trigger the non-physiologic bi-directional contractile wave propagation of the target smooth muscle such as the ureter. This ensures that impulse peak will reach the target voltage and current in the preset impulse width. Impulses may be delivered by the novel system at set intervals to allow the user to keep the actuating button depressed while touching the functional tip of the system to parts of the abdominal wall until target tissue is close enough to be stimulated for visible contraction.

In the preferred embodiment, the system will typically generate short current pulse(s) of approximately 10 microseconds to 20 milliseconds in total signal duration (but which may be as long as 500 milliseconds) with single activation. By holding down the trigger, the system will continue to discharge impulse(s) at 0.5 to 1 hertz increments continually until release. The system's waveform may vary depending on the embodiment. In embodiments where the system is likely to be powered and tethered to a power generator, the waveform may be sinusoidal, 1 to 600 kilohertz in frequency (preferentially below 100 kilohertz to optimize tissue reactivity), and with the total signal duration being again in the 10 microsecond to 20 milliseconds range (up to 500 milliseconds) which would ideal for muscular contraction without resulting in tissue injury.

Figure 4:
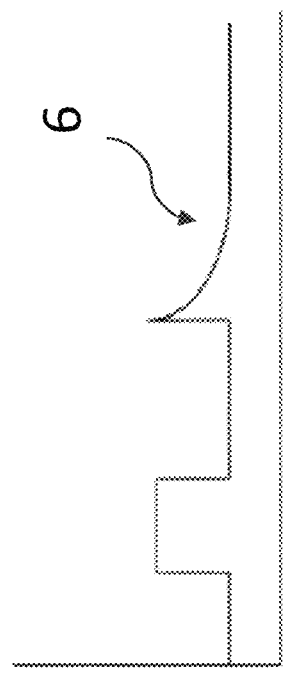
FIG. 4—Monophasic square and capacitor discharge waveforms of a single stimulating electrical pulse.

To reduce the risk of tissue injury, the peak voltage of system will be maintained at or below 500 volts, with the current at or below 1 ampere with a 550 ohm load setting. The voltage will typically be at least 5 volts with the same load, as this would not be sufficient in serving to trigger the contractile wave propagation in smooth muscle tissue. Unlike other stimulation systems, these stimulation systems will typically be voltage controlled to effectively deliver a pulse capable of generating a visible, smooth muscle contraction. Skeletal nerve stimulation is typically performed with current as a primary controlled factor (e.g. current driven) in generating a nerve/skeletal muscle response as previously described, wherein tissue resistance experienced is greater than 1000 ohms. These nerve/skeletal muscle stimulation devices, operating against a lower intracorporeal tissue resistance, e.g. less than 1000 ohms, will not deliver a voltage sufficient to elicit a smooth muscle contraction. In contrast, by using voltage control, the system of the present invention, assures sufficient voltage is delivered into the lower tissue resistance found with intracorporeal smooth muscle tissues to elicit a visible response. When set for an approximately 550 ohm load, the system of the present invention device can deliver at least 6 volts, 7 milliamps, with a charge greater than 30 microcoulombs and an energy of greater than 0.05 millijoules with a capacitor discharge waveform 6 (FIG. 4).

Voltage and current in the bipolar version of the system can be safely applied to target tissues without concern of cardiac arrhythmic stimulation since the electrical impulse travels between the electrodes only a short distance apart from each other (on the order of millimeters) and is of an extremely brief duration. In a monopolar system design, the electrical power is rapidly diffused from the hand held portion of the device on through the grounding pad again providing safe passage of the electrical signal.

The current powering the handheld system in one embodiment would be DC current, as in one preferred embodiment the system would be battery powered, single use and fully disposable. In the tethered system, the expected current would be initially AC with subsequent signal conversion prior to impulse discharge into target tissues.

In this or other embodiments, the impulse may be of a curvilinear degeneration similar to a capacitor discharge 7

Figure 5:
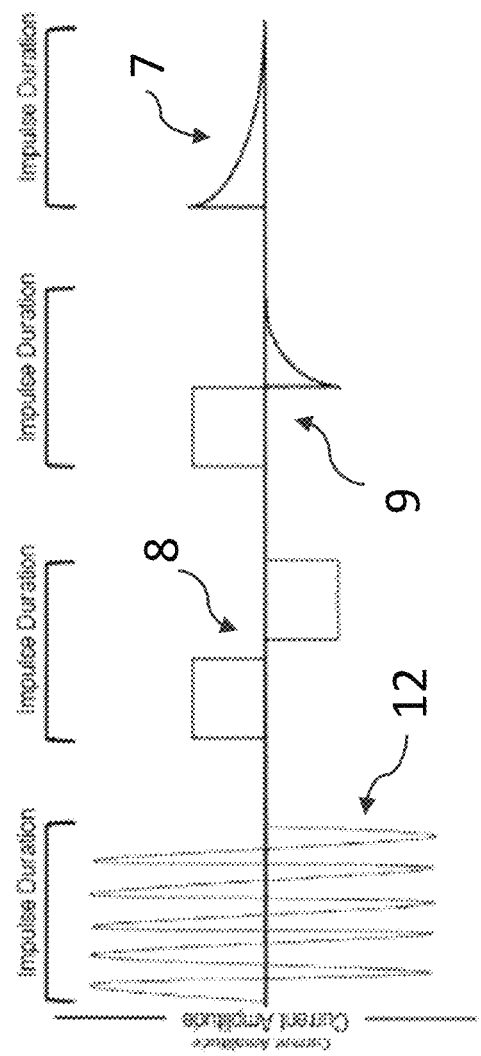
FIG. 5—Sinusoidal, symmetric and asymmetric waveforms along with monophasic capacitor discharge waveform of a single stimulating electrical pulse.

(monophasic). The impulse waveform may also have a square wave component to it, and as such may form a balanced or unbalanced, symmetric 8 or asymmetric 9 biphasic waveform. The waveforms generated by the novel system would not be limited to these, and may be tailored for targeting different types of target tissues depending on their response ranges, distance away from impulse discharge, and thickness/quality/resistance of tissues in between target tissues and proposed system (FIG. 5).

In a preferred embodiment, the waveform will be one of a capacitor discharge as this closely mimics physiologic action potentials within muscles and nerves. As square wave impulses are less physiologic in character, application of a square wave for smooth muscle stimulation requires an increased voltage and is less preferred. The minimum voltage for smooth muscle stimulation using a capacitive discharge waveform is typically 6 volts with signal duration of 2.2 millisecond decay constant (time to 1/e discharge, or approximately 36.8% of the initial voltage). In contrast, minimum voltage for smooth muscle stimulation using a square waveform is typically 15 volts with signal duration of 1000 microseconds Voltage levels also need to be increased as signal duration decreases. The same requirements are present for symmetric and asymmetric biphasic waveforms.

The capacitor discharge waveform has been found to require a lower voltage than other tested waveforms, resulting lower current and power requirements than other waveforms. This is particularly advantageous for battery-driven designs as described herein as well as for integrating the technology into another instrument where space for insulating the stimulation wiring may be limited. An "undriven" capacitor discharge waveform relies on the inherent discharge of voltage degradation/time constant from capacitors in a closed circuit and was found to be more efficacious in eliciting the response than a use of "driven capacitor discharge" waveform (e.g. matching a specific voltage degradation curve using a function generator).

An alternative preferred "Voltage Driven" circuit assures the voltage, which is the primary influencing factor, elicits a smooth muscle response and is always within the preferred range and that the resulting current varies dependent upon the load (tissue) resistance. Prior art nerve stimulators use a "current driven" circuit design which causes a significant drop in resulting voltage when used with low load (tissue) resistance as found with moist, intracorporal tissues.

Table 1 below provides exemplary and preferred operational parameters for tissue stimulation using a monophasic, undriven capacitor discharge waveform:

TABLE 1

| Parameter | Defined | Broad Range | Preferred Range |
| --- | --- | --- | --- |
| V-Voltage, Peak (input) | Measured peak voltage, combined with a current not to exceed 1 A, across a 550 Ohm load (tissue) resistance. | 5 V-500 V | 6-60 V |
| I-Current, Peak(output) | Not to exceed 1 A across a 550 Ohm load (tissue), the actual value is the resultant of the voltage, charge and tissue resistance at the site of stimulation | <1 A | 5 mA-125 mA |
| Q-Charge (input, Coulombs = ampere-seconds) | Amount of capacitive charge in the circuit released at the time of pulse initiation | >30 μC | 40 μC-450 μC |

TABLE 1-continued

| Parameter | Defined | Broad Range | Preferred Range |
| --- | --- | --- | --- |
| E-Energy (output) | Amount of energy generated per pulse, the actual value is the resultant of the voltage, charge and tissue resistance at the site of stimulation | >0.05 mJ | 0.05 mJ-9 mJ |
| T-Time, Duration (input) | Decay constant (time to 1/e discharge or 36.8% of the initial voltage) | 10 μs-20 ms | 100 μs-4 ms |
| F - Frequency of repetitive pulses (input) | When button held down, continued discharge at | 0.5-1 Hz | 0.5-1 Hz |

Table 2 below provides exemplary and alternative operational parameters for a voltage-driven tissue stimulation using a monophasic, square waveform:

TABLE 2

| Parameter | Defined | Broad Range | Preferred Range |
| --- | --- | --- | --- |
| V-Voltage, Peak (input) | Measured peak voltage, combined with a current not to exceed 1 A, across a 550 Ohm load (tissue) resistance. | 10 V-500 V | 15 V-100 V |
| I-Current, Peak (output) | Not to exceed 1 A across a 550 Ohm load (tissue), the actual value is the resultant of the voltage, charge and tissue resistance at the site of stimulation | <1 A | 30 mA-200 mA |
| Q-Charge (input, ampere-seconds) | Amount of capacitive charge in the circuit released at the time of pulse initiation | >30 μC | >100 μC |
| E-Energy (output) | Amount of energy generated per pulse, the actual value is the resultant of the voltage, charge and tissue resistance at the site of stimulation | >0.05 mJ | >3.5 mJ |
| T-Time, Duration (input) | Length of Pulse | 10 μs-20 ms | 10 μs-500 ms |
| F - Frequency of repetitive pulses (input) | When button held down, continued discharge at | 0.5-1 Hz | 0.5-1 Hz |

In a preferred embodiment, the voltage and current generator along with all other electrical settings of the system will typically not be user adjustable, and will be at a locked setting both to ensure system efficacy, and to ensure patient safety. These settings, as well as the button, LED(s), and other electronic components will be set into a printed circuit board inset into the handle of the system. The system in one preferred embodiment will be powered by at least one battery (12-Volt or otherwise) not only for generator requirements, but also to maintain the low-profile, cylindrical shape of the handle. Having an internal power source also maintains a stand-alone system that does not require any cables or cords for grounding or power in this embodiment. As the system will be intended for single-use, a power-off switch will be absent, and in one preferred embodiment, the system will be activated by removing a nonconductive pull-tab that serves as a physical boundary to completing the circuit in the handle of the system while being stored before use.

In a preferred embodiment, the system would provide visual cues not only of the status of the power source, but also of when electrical stimulation is applied at the functional tip of the device. These may be light emitting diodes (LEDs) visible on the end of the system held by the operator or operating assistant 10. In one preferred embodiment, one LED will turn on when system is actuated in such a way that the LED will be on during impulse delivery and then turn off. A second LED will remain on the entirety of the time the system is powered, and will turn off when the DC power source is no longer capable of generating an impulse of the specified voltage and current.

The end of the system of the present invention that interfaces with the smooth muscle target is comprised of no fewer than two electrodes so that the system is of a bipolar design. Contacting tissue completes the circuit, and the electrical impulse is delivered from the body of the system, down the shaft, through the abdominal wall and through the tissue in a matter triggered by the operator(s). When the system comes in close enough contact with target smooth muscle such as the ureter, and the electrical impulse is sent to that tissue, it will generate a bi-directional full length contraction of the ureter that will be visible on the video screen for the operator, or directly in the field of view in an open surgical procedure.

With the system of the present invention, there is enough tissue penetration by the electrical stimulation caused by the generation of an electrical field to initiate the target tissue contraction. This effect will then be visible to the operator on the video monitor even without deep tissue dissection, as the path of the ureter can be seen as movement translated to the overlying tissues. The main limitation to visualization in this case is the thickness of these overlying tissues as the electrical stimulation has a depth of penetration that likely exceeds visible movement translation. In addition, the unique setting of minimally invasive surgery is one where the patient's skeletal muscle is chemically paralyzed as to allow for maximal expansion of the now-paralyzed abdominal wall. The paralytic agents used in the operating room do not affect smooth muscles such as intestines and ureters. As such, the system of the present invention is extremely specific in stimulation, and subsequent visual identification of smooth muscles such as the ureter, since all nearby skeletal muscle is unable to respond to the system's stimulatory signals. This is a unique feature and application of our system that would not be obvious to those skilled in the art.

Higher voltage pulse stimulation, e.g. higher than 50V, would be clinically undesirable in extremity, orthopedic, ENT or other open surgery due to the patient's skeletal muscles and nervous system response, e.g. an involuntary reflex (jerk, jump or twitch) on the operating table. Using higher voltage pulse stimulation as described herein is clinically acceptable in laparoscopic, robotic, NOTES, or other minimally invasive surgeries due to the concurrent administration of the paralytic anesthetic agents, used to relax the skeletal muscles and nerves and by doing so, suppresses their responses to higher voltage stimulation. As smooth muscle structures are not affected by these agents, the visual response from higher voltage stimulation assures it is a smooth muscle structure that responds, minimizing any confusion as to the anatomical structured interrogated.

To ensure successful target tissue stimulation, and remain as a potential stand-alone system, the functional tip of the system of the present invention will have no fewer than two electrodes spaced a minimum of 1 millimeter apart. The electrodes will be insulated from each other and the remainder of the system, and separated proximally in one embodiment by nonconductive, synthetic, polymer based material to prevent electrical arcing. In one preferred embodiment, these electrodes are connected to the circuit board and the power source in the handle of the system via conductive wires that are individually shielded to prevent electrical shorting or arcing not only to each wire, but to the shaft of the system as well. The shaft of the system would be constructed of a stiff, nonconductive tubular material such as polyamide, or of an insulated metal (such as stainless steel with polymer coating) to prevent unintended electrical signal transfer.

The human ureter is on average 3 millimeters wide, and as such the electrodes on the tip of the system of the present invention will in one preferred embodiment be spaced approximately 3 millimeters apart and oriented perpendicularly to the linear pathway of the ureter 11. This results in an electrical stimulation that traverses the ureter in a transverse plane, with an electrical field generated between the electrode tips of the bipolar arrangement, and as such triggers the smooth muscle in a plane that matches physiologic signal propagation (FIG. 6).

With further reference to FIG. 5, excitatory current for smooth muscle stimulation according to the present invention may be delivered with a variety different waveforms or shapes as viewed on an oscilloscope. The described waveforms may all be adjusted to elicit a ureter contractile response as well as smooth muscle contraction in other organs and parts of the body.

A sinusoidal waveform 12 suitable for smooth muscle stimulation according to the present invention would typically have a frequency below 100 kHz (frequencies above that value are typically ineffective and potentially injurious). This waveform can be adjusted to parameters that are non-injurious and are optimized for smooth muscle stimulation allowing for ease of instrument integration.

Symmetric, balanced waveforms 8 (FIG. 5) with defined positive and negative components in the form of matched square waves may also be used for smooth muscle stimulation according to the present invention. An exemplary wave would have a positive square pulse followed by an equal negative square pulse, providing a fully controlled, balanced waveform that would avoid a deleterious buildup of net charge, avoiding potential burns and injury to the engaged tissue.

An asymmetric, balanced waveform 9 (FIG. 5) having defined positive and negative components, e.g. one square wave and a capacitor discharge waveform as the balancing component, may also be used for smooth muscle stimulation according to the present invention. Such a balanced waveform would also minimize or avoid and buildup of net charge. Such biphasic impulses would preferably have an active phase that has a positive amplitude with current traveling through the cathode into the tissue, where the balancing phase would have current return through the anode. Such an asymmetric, balanced waveform could be optimized not only for smooth muscle stimulation but also for nerve stimulation (as neurons respond more readily to negative current signals).

Additionally, monophasic waveforms 7 (FIG. 5), such as the capacitor discharge and square wave signals described previously, when discharged in brief bursts, would be effective in eliciting target tissue contraction, have a net charge that can be optimized into a set impulse duration, and present minimum risk of injury to target tissues.

In other aspects, a functional tip of the system of the present invention may be devoid of angular points, needles or cutting edges as to avoid iatrogenic injury, and also to allow the system to be used as a blunt dissector or probe. The tip may be a pair of electrodes configured with rounded external features 13, consist of a ring and a point electrode 14 for a streamlined, atraumatic tip that has an omnidirectional ability to stimulate target tissues, or be physically separated in a Y configuration 15, all in the case of bipolar design among any other potential configurations designed to fit through a 5 mm trocar shaft (FIG. 7). The surface areas of the electrodes will be adequate to maintain appropriate current density for desired stimulation of target tissues. In any possible permutation of tip design, there will always be the ability for the electrons to flow from one electrode to another when the circuit is completed via tissue contact, thus resulting in the desired tissue response. The bipolar design would in one embodiment ensure safe electrical impulse control and localization.

Systems of the present invention may be mounted in tandem, or integrated into a camera system used in minimally invasive surgery or robotic surgery. The system of the present invention may also be implemented with a flexible, malleable, steerable, and/or rigid linear or curved shaft in such a way as to be used in endoscopic procedures, catheter-based percutaneous procedures, natural orifice surgical approaches, or otherwise incorporated into robotic systems used in procedure or operating rooms. The shaft of the instrument may either have a flexible neck segment, or be completely flexible. The system of the present invention may also be combined with other existing surgical instruments either as an interchangeable tip that may be advanced or retracted on demand by the user, or remain in place as an integrated part of the existing instrument that may then be activated by the user, or may be incorporated into the instrument's existing features.

To increase surgeon efficiency and to provide a closer to real-time method of detection of the ureter, the systems of the present invention may also be integrated into electrosurgical and other instrument used in open or minimally invasive surgery, such as graspers, scissors, suction irrigators or other dissection instruments. Such embodiments will usually have stimulation controls separate from the deployment and activation mechanisms used for cutting or cauterizing effects of the electrosurgical tool as to ensure the physician can safely distinguish between stimulation and treatment. In one embodiment, a probe with the bipolar tip 16 may be reversibly extended from the functional end of the electrosurgical instrument with a lever 17, and a button depressed to generate the stimulatory effect. This would ensure a purposeful and safe distinction between stimulation and cut/cautery (FIG. 8). In another embodiment, the bipolar tip is implemented by each of the two fingers of a grasper acting as the individual electrodes spatially separated during use to mimic the required separation distance for proper use.

In an embodiment of the system of the present invention where the device is connected to a power generator 18 either on or off of the surgical field (i.e.—paired or connected to another electrosurgical instrument platform), the functional tip of the device may also be an atraumatic single electrode 19. Since the patient will already have a grounding pad 20 attached to their body for the other electrosurgical instrument(s) usage, stimulation of target tissues can be performed in a monopolar fashion as the circuit will be completed through the body. In this version, the functional tip of the device would preferentially be the cathode. If desired in an embodiment, the functional tip of the device may remain bipolar (even if integrated into a monopolar electrosurgical instrument platform) for more focused impulse delivery that may require less energy and power (FIG. 9). In either embodiment, the stimulatory signal may be triggered on the hand held component of the system via a switch, or using an alternate switch such as a foot pedal.

Figure 10:
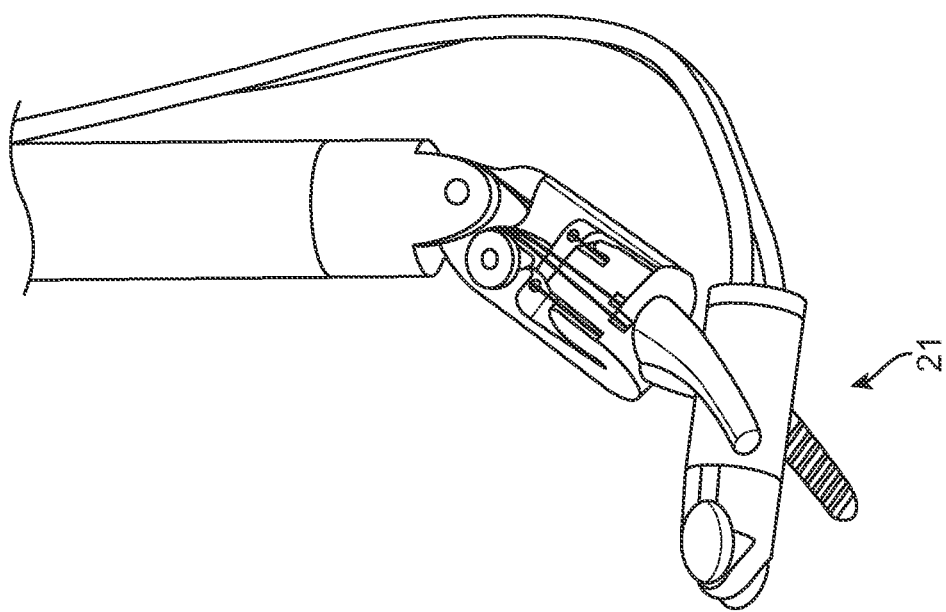
FIG. 10—Device embodiment with smaller end effector that may be grasped, manipulated or integrated into robotic arms.

With an understanding of the novel, defined energy parameters and system functional tip requirements, the system of the present invention may be integrated into minimally invasive, or open surgical devices and systems that are either inherently powered, or may have attachments to power them for this stimulatory function. In an automated, or robotic setting where the care provider is operating at a console or otherwise in an indirect fashion, the system of the present invention may be place into or onto one arm of the operating equipment in a reversible or irreversible fashion based on hardware design. It may also be a separate component 21 that is grasped by the robotic platform (FIG. 10). In this embodiment, the tip configuration would be similar to the hand held version of the system, but the shaft length may be shortened to allow for greater intracorporeal maneuverability (especially when operating in spaces such as the pelvis). If the operating equipment already requires a grounding pad be placed on the patient, the functional tip of the system of the present invention may be constructed in a monopolar fashion with a single electrode tip. Stimulation initiation would be triggered either with a hand controller or foot controller based on the surgeon interface. An audio and/or visual cue would also be present to inform the operator that an electrical impulse was being delivered.

With power profiles intended for smooth muscle stimulation, the system of the present invention is not only applicable in generating non-physiologic, visible contractile response to the ureters, but also for other structures that contain smooth muscle tissues. In assisting placement of gastric pacer electrodes within key parts of the stomach wall, the system can first be used to ensure that the intended innervated (or poorly innervated) sections of the stomach can and will respond to electrical stimuli as expected. The system can then be used to facilitate accurate placement of more permanent electrodes into and onto the stomach.

In cases of intestinal diseases such as Hirschprung's where the colon lacks innervation to certain portions, an intracorporeal stimulator may be used to determine at what level and what part(s) of the colon do and do not respond to excitable stimuli. This can assist the operator(s) in determination to what level, and at what level any potential surgical intervention may need to be done, and may allow for more precise resections and maximal tissue preservation. The same approach may also be used for the smooth muscle portions of the esophagus to identify functionally responsive and less responsive tissues or sections.

There is also the ability for the system to assist in identification of the location and pathways that nervous tissue may take as well in the intracorporeal setting such as the obturator nerve in pelvic procedures where the tissue planes are distorted due to tumor or scarring. With the tissue penetrating signal from the system, nervous tissue can also be stimulated in a non-paralyzed setting, and thus let the operator(s) know where nervous tissue that they may want to avoid is located even without direct visualization.

As shown in FIG. 11, the stimulators of the present invention may be incorporated into surgical instruments, such as powered electrosurgical tools and/or grasper/dissector tools. When incorporated into electrosurgical/electrocautery tools, the stimulators may have an end effector 22 on or at a distal region or tip of a shaft that is insulated and may be parallel or incorporated with the other electromechanical components of the instrument. The end effector may be either fixed in place, or more preferably be able to be extended and retracted with a lever 23 or other actuating mechanism. This provides the surgeon with the flexibility of having multiple powered surgical instrument features in a single device, and would increase operating efficiency since there would not be a need to do an instrument exchange multiple times during an operation.

As shown in FIGS. 12A and 12B, the stimulators of the present invention may alternatively be incorporated into grasper/dissector tools where the jaws 24 function as the anode and the cathode thus permitting the effector end of the instrument to deliver the stimulatory electrical impulses as well as to provide the desired surgical function. In this embodiment, the novel stimulator's power and impulse generation component 25 may be reversibly or irreversibly attached. The stimulator may also be integrated into or grasped by a robotic surgical platform's instruments. Since the surgeon would be operating the robotic platform from a console, the stimulator would typically be grasped, manipulated and otherwise positioned by the robotic surgical platform's arms.

As shown in FIG. 13, a handheld component 26 may be powered via an off-field, programmable electrical generator. Advantage of using such remote generators include that they are commonly present in most operating rooms and able to convert line voltage into programmable waveforms and adjustable signal intensities. When powered a remote generator, the hand-held component be made lighter, have a thinner profile, and be more cost efficient since enclosed batteries and circuit components will no longer need to be fully housed in the handle. Powering the systems of the present invention with a generator could also facilitate user adjustable impulse frequency, intensity, waveform and signal duration changes made while the non-tethered embodiment will often have fixed features.

As shown in FIGS. 14A and 14B, an end effector may be bipolar allowing the system of the present invention to operate in a stand-alone mode or be powered with a remote generator, potentially eliminating the need for a grounding or dispersive pad attachment to the patient. The tip will typically have a diameter no wider than 6 mm to allow for introduction through a working channels or lumen of other instruments, trocars, and the like. The end effector of such bipolar instruments may have two blunt/flat electrodes physically separated by nonconductive material and/or space. This ensures the delivered electrical impulse is optimally delivered into target tissues. Depending on the embodiment, the electrodes may encompass part of the circumference of the distal tip 27 (FIG. 14B) of the device, or otherwise follow the contours of the device end 28 (FIG. 14A) to minimize angles, allow for safe maneuvering around delicate tissues, and have been optimized for manufacturability.

The system described may be applied in any minimally invasive process where the instruments are inserted through the body wall towards target tissues (as well as applied in open thorax or abdomen procedures). The minimally invasive processes may be either performed by (an) operator(s) handling the instruments directly as they stand next to the patient in the operating room, or by (an) operator(s) interfacing with a surgical system that interfaces with the patient.

What is claimed is:

1. A method for inducing an observable response in a target anatomy comprising smooth muscle cells during a medical procedure, said method comprising:

providing an electrical stimulator coupled to at least one electrode;

manually engaging the at least one electrode against a target tissue;

delivering a plurality of stimulatory electrical pulses from said stimulator to the at least one electrode, wherein each stimulatory electrical pulse comprises an undriven capacitive discharge consisting of an initial discharge with an exponential waveform having a time constant equal to a product of an uncontrolled tissue resistance and a capacitance of a capacitor in a closed circuit with the target tissue proximate the target anatomy; and observing the target tissue to detect a response in the target anatomy induced by the electrical stimulation energy.

2. A method according to claim 1, wherein the undriven capacitive discharge has a peak voltage in a range from 5V to 500V.

3. A method according to claim 2, wherein a peak voltage is in a range from 6V to 60V.

4. A method according to claim 2, wherein the undriven capacitive discharge has a resultant variable current less than 1 A.

5. A method according to claim 4, wherein a resultant variable current is in a range from 5 mA to 125 mA.

6. A method according to claim 4, wherein the undriven capacitive discharge is greater than 30 μC.

7. A method according to claim 6, wherein the undriven capacitive discharge is in a range from 40 μC to 450 μC.

8. A method according to claim 6, wherein each undriven capacitive discharge has a total resultant energy greater than 0.05 mJ.

9. A method according to claim 8, wherein each undriven capacitive discharge has a total resultant energy in a range from 0.05 mJ to 9 mJ.

10. A method according to claim 8, wherein each undriven capacitive discharge has a decay constant duration in a range from 10 μs to 20 ms.

11. A method according to claim 10, wherein the duration is in the range from 100 μs to 4 ms.

12. A method according to claim 10, wherein consecutive undriven capacitive discharges are delivered at a rate from 0.1 Hz to 2 Hz.

13. A method according to claim 12, wherein consecutive undriven capacitive discharges are delivered at a rate from 0.5 Hz to 1 Hz.

14. A method according to claim 12, wherein the target anatomy is selected from the group consisting of a ureter, a bladder, stomach, esophagus, and an intestine.

15. A method according to claim 12, wherein the electrical stimulator comprises a shaft having at least one electrode and delivering electrical stimulation comprises advancing the shaft to engage the at least one electrode against the tissue proximate the target anatomy.

16. A method according to claim 15, wherein said shaft is advanced through a trocar, cannula, an endoscope, or a catheter.

17. A method according to claim 15, wherein said shaft is advanced through or concurrently with a surgical tool.

18. A method according to claim 15, wherein said shaft is advanced using graspers.

19. A method according to claim 15, wherein said shaft is advanced by a robot.

20. A method according to claim 12, wherein the parameters of said undriven capacitive discharges are adjustable by a user.

21. A method according to claim 12, wherein the parameters of said undriven capacitive discharges are preset.

22. A method according to claim 12, wherein the capacitive discharge is bipolar.

23. A method according to claim 12, wherein the capacitive discharge monopolar.

24. A method according to claim 12, wherein the target anatomy comprises a ureter, further comprising visually observing the contraction of tissue to determine the path of a ureter in the tissue.

25. An electrical stimulation system for inducing an observable response in a target anatomy comprising smooth muscle cells during a medical procedure, said electrical stimulator comprising:

a stimulator having at least one electrode; and a power supply connectable to said at least one electrode and configured to deliver electrical stimulation energy through said stimulator to tissue proximate the target anatomy, wherein the stimulation energy comprises a plurality of stimulatory electrical pulses, each pulse consisting of an undriven capacitive discharge comprising an initial charge which discharges with an exponential waveform having a time constant equal to a product of an uncontrolled tissue resistance and a capacitance of a capacitor in a closed circuit with a tissue proximate the target anatomy.

* * * * *